United States Patent [19]

Cox

[11] Patent Number: 4,606,260
[45] Date of Patent: Aug. 19, 1986

[54] MOVEABLE WELDING STATION

[76] Inventor: Donald G. Cox, 14 Briar Patch Rd., Bargersville, Ind. 46106

[21] Appl. No.: 764,085

[22] Filed: Aug. 9, 1985

[51] Int. Cl.⁴ .............................................. B05B 15/12
[52] U.S. Cl. ............................ 98/115.3; 55/DIG. 18; 55/385 B
[58] Field of Search ................. 98/115.1, 115.3, 115.4; 55/385 B, DIG. 18

[56] References Cited

U.S. PATENT DOCUMENTS

| | | | |
|---|---|---|---|
| 2,436,508 | 2/1948 | Fairbanks | 98/115.4 |
| 2,604,840 | 7/1952 | Looli et al. | 98/115.4 |
| 3,121,618 | 2/1964 | Yerzley | 98/115.4 |
| 4,091,719 | 5/1978 | Galloway | 98/115.1 |
| 4,245,820 | 1/1981 | Muryn | 98/115.4 |
| 4,287,405 | 9/1981 | Ohmae et al. | 98/115.4 |

*Primary Examiner*—Ronald C. Capossela

[57] ABSTRACT

A moveable welding station. An exhaust hood mounted atop a pair of depending legs with a welding curtain extending downwardly from the hood and defining the work area. An exhaust fan mounted to the hood pulls air upwardly from the work station through a bottom slot and then radially into a plurality of cylindrical air filters. An air passage is provided from the hollow central portions of the cylinders upwardly through a pair of charcoal filters exiting into the ambient air surrounding the welding station. A second source of pressurized air is directed via air tubes into the hollow central portions of the cylindrical filters in a direction opposite of the normal air flow in sequential pulsed fashion dislodging foreign particulate matter from the cylindrical filters. A dust pan removably mounted to the hood receives the foreign particulate matter allowing for the automatic cleaning of the filter.

16 Claims, 5 Drawing Figures

MOVEABLE WELDING STATION

BACKGROUND OF THE INVENTION

This invention is in the field of welding stations and more specifically those employing exhaust hoods for the removal of noxious gases from the welding station.

DESCRIPTION OF THE PRIOR ART

Various manufacturing processes including welding as well as combining various chemicals result in noxious by-products. As a result, it is the custom to provide an exhaust hood extending over the entire work area for the removal of the noxious fumes. Typically, the noxious fumes are exhausted externally of the building resulting in considerable heat loss depending upon the outside temperature. I have therefore designed an exhaust apparatus which will recirculate air between the work station and the ambient air within the building. Further, the exhaust apparatus is designed to incorporate a work area for a single worker as compared to the prior multiple work station exhaust devices. As such, the exhaust apparatus is relatively light weight and may be moved within the building depending upon the particular work requirements.

It is also customary to provide a central exhaust system connected to a variety of work area hoods limiting the portability of the device. The apparatus disclosed herein incorporates an exhaust system independent of other work areas and permanent building fixtures.

Through extended use, the removable filters within the exhaust passage become clogged with foreign particulate matter and must be periodically cleaned. In order to eliminate the necessity for shut down procedures, I have incorporated a backcharge pulsing system to reverse the normal air flow through the filters dislodging the foreign particulate matter which is then directed into a collection container. The filters are arranged into groups of filters which are sequentially cleaned allowing for the remaining filters to continue their normal operation. Means are provided to prevent the dislodged foreign particulate matter from passing between different groups of filters.

SUMMARY OF THE INVENTION

One embodiment of the present invention is an air treatment and recycler for a single welding station within a building comprising a frame forming a hood and configured to form a single welding station, the frame including an air passage having an entrance opening within the single welding station and an exit opening on the frame and into ambient air within the building, curtain means mounted to the frame and depending therefrom surrounding the single welding station on at least two sides thereof, a motorized fan mounted to the frame operable to draw air from within the single welding station through the passage and forcing the air outwardly of the frame recirculating air between the welding station and ambient air within the building, first filter means mounted in the passage and operable to filter air moving in a normal direction therethrough, pulsing means operably associated with the filter means and operable to direct pulses of pressurized air flow in a direction opposite from the normal direction and of a magnitude greater than the air moving in the normal direction through the filter means unlodging foreign particulate matter from the filter means, and, holding means mounted to the frame and positioned to receive the foreign particulate matter from the filter means as the pulsing means unlodges same.

Another embodiment of the present invention is an air treatment and recycler for a work station comprising a frame forming a hood and configured to form a work station, the frame including an air passage having an entrance opening within the work station and an exit opening on the frame, curtain mounting means on the frame to receive curtains depending therefrom to at least partially surround the work station, exhaust means mounted to the frame operable to draw air from within the work station through the passage and forcing the air outwardly of the frame recirculating air within the work station, first filter means mounted in the passage and operable to filter air moving in a normal direction therethrough, pulsing means operably associated with the filter means and operable to direct pulses of pressurized air flow in an direction opposite from the normal direction and of a magnitude greater than the air moving in the normal direction through the filter means unlodging foreign particulate matter from the filter means, and, holding means mounted to the frame and positioned to receive the foreign particulate matter from the filter means as the pulsing means unlodges same.

Yet a further embodiment of the present invention is an exhaust hood for recirculating air from beneath the hood to the air surrounding the hood comprising upstanding frame members to support a curtain defining the work area, a hood frame mounted atop the frame members with the hood frame including an air passage with an air entrance opening beneath the hood frame and an air outlet opening outwardly thereof, air moving means in communication with the air passage and operable to move air therethrough drawing air surrounding the hood into the work area and then expelling same into the air surrounding the hood, filters mounted to the hood frame and operable to filter air moved by the air moving means through the air passage, pulsing means positioned adjacent the filters and operable to pulsatingly force air through the filters in a direction opposite to air moved by the air moving means dislodging foreign matter in the filters, and, back charge baffle means operable to limit foreign matter flow between filters.

It is an object of the present invention to provide a new and improved moveable welding station.

Yet another object of the present invention is to provide a self-standing exhaust apparatus which is independent of a central exhaust system and building fixtures.

A further object of the present invention is to provide a moveable welding station having a single work area and means for circulating air between the work area and the ambient air within the building containing the device.

In addition, it is an object of the present invention to provide an air filter system with means for directing reverse air flow through the filters dislodging foreign particulate matter and limiting the flow of foreign particulate matter between filters.

Related objects and advantages of the present invention will be apparent from the following description.

DESCRIPTION OF THE PREFERRED EMBODIMENT

Figure 1:
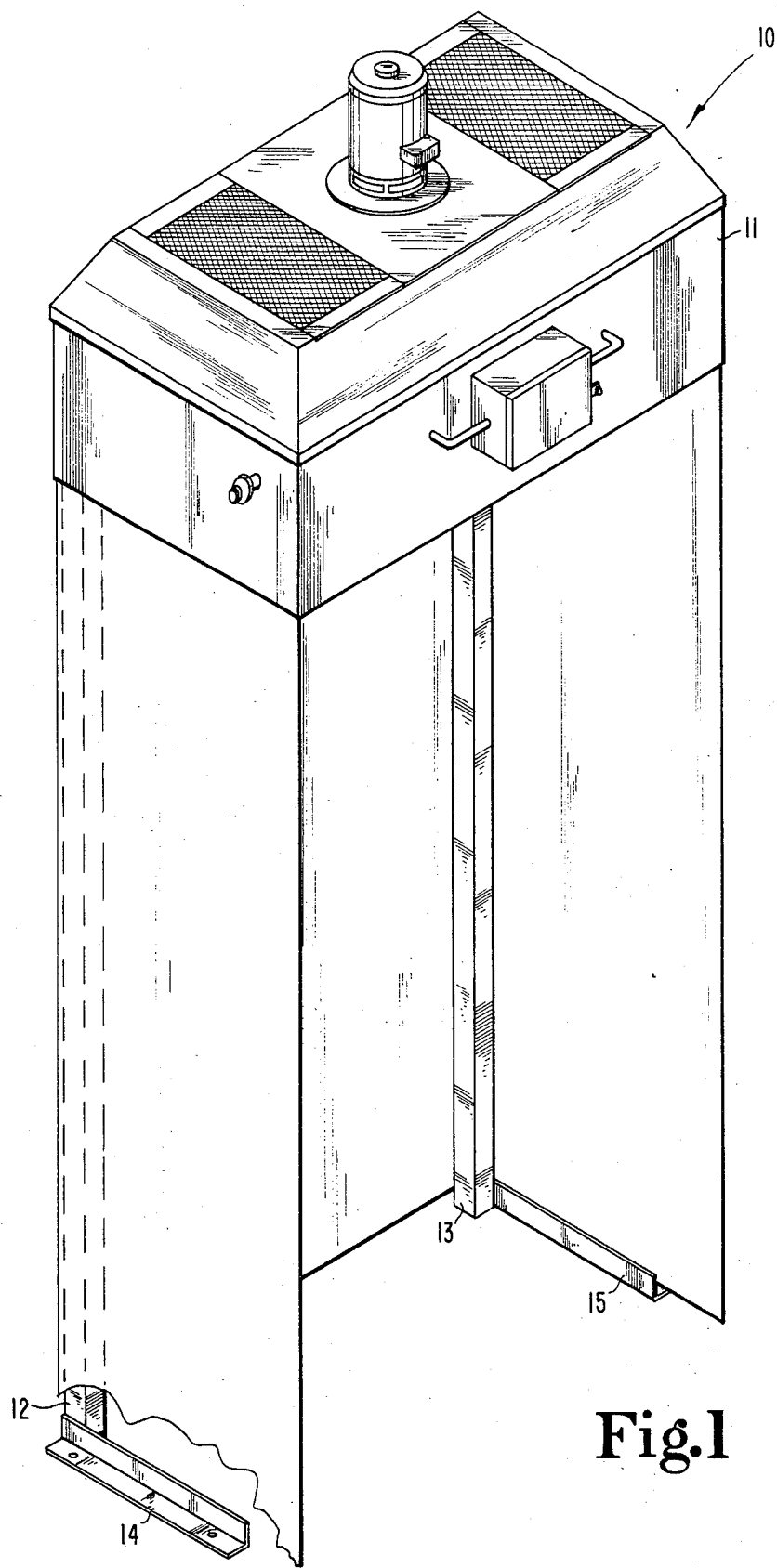
FIG. 1 is a prospective fragmentary view of the moveable welding station incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown a moveable welding station 10 including an exhaust hood 11 with a pair of downwardly extending legs 12 and 13 secured thereto. Fixedly mounted to the bottom end of legs 12 and 13 are a pair of horizontally extending frame members 14 and 15 which may be removably secured to the floor of the building in which the station is positioned.

Figure 2:
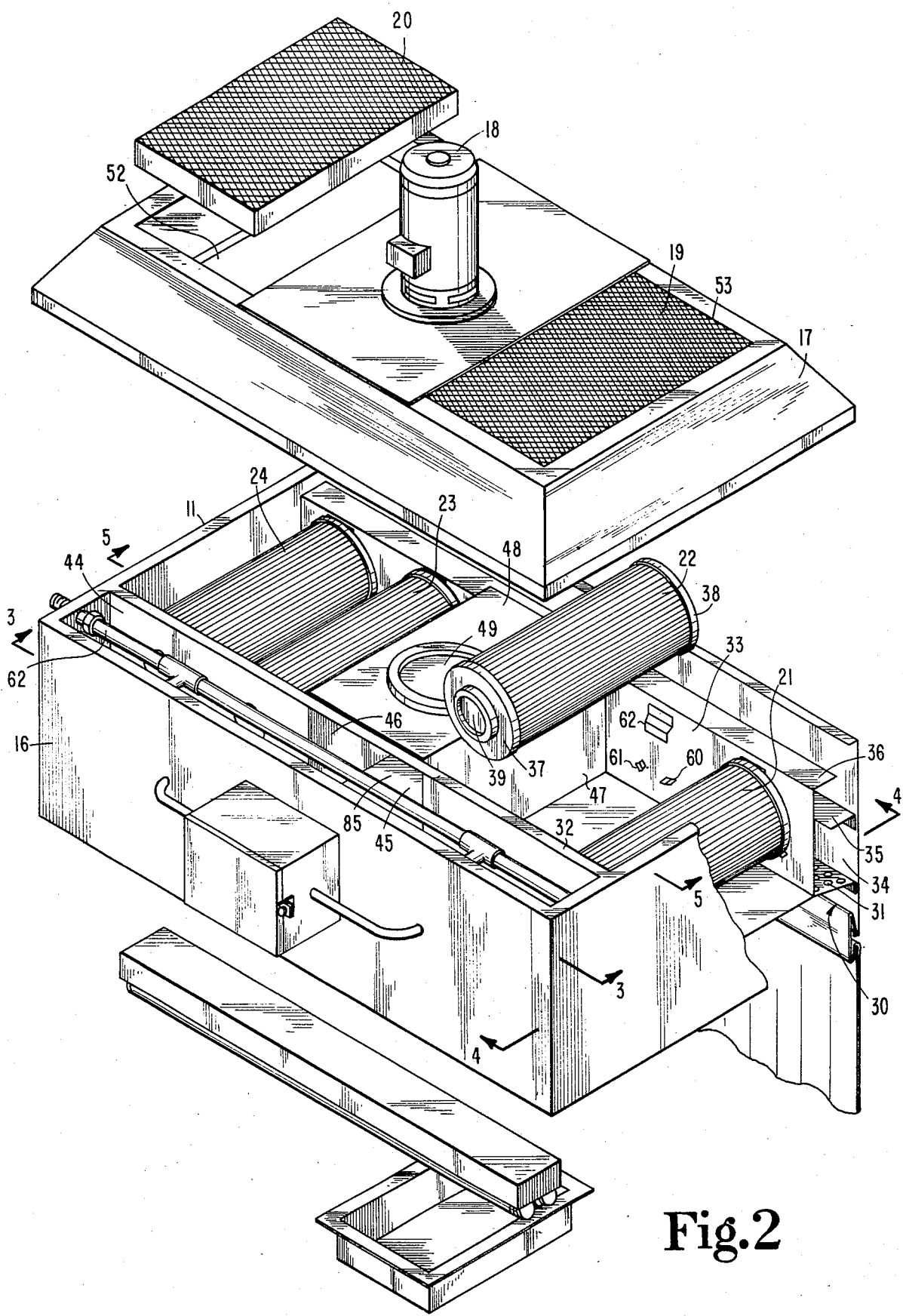
FIG. 2 is an enlarged exploded perspective view of the exhaust hood.

Hood 11 (FIG. 2) includes a rectangular frame enclosure 16 upon which is hingedly mounted a lid 17. A three-quarter horse power electric fan motor 18 is mounted to lid 17 and is positioned between a pair of filter cartridges 19 and 20 through which the filtered exhaust air flows into the ambient air within the building. Four additional filters 21, 22, 23 and 24 are each provided with a cylindrical configuration and are removably mounted within the rectangular housing 16 and provide filtering of the air which is circulated from the area beneath the exhaust hood and eventually out through charcoal filters 19 and 20 to the ambient air surrounding the moveable welding station.

Figure 3:
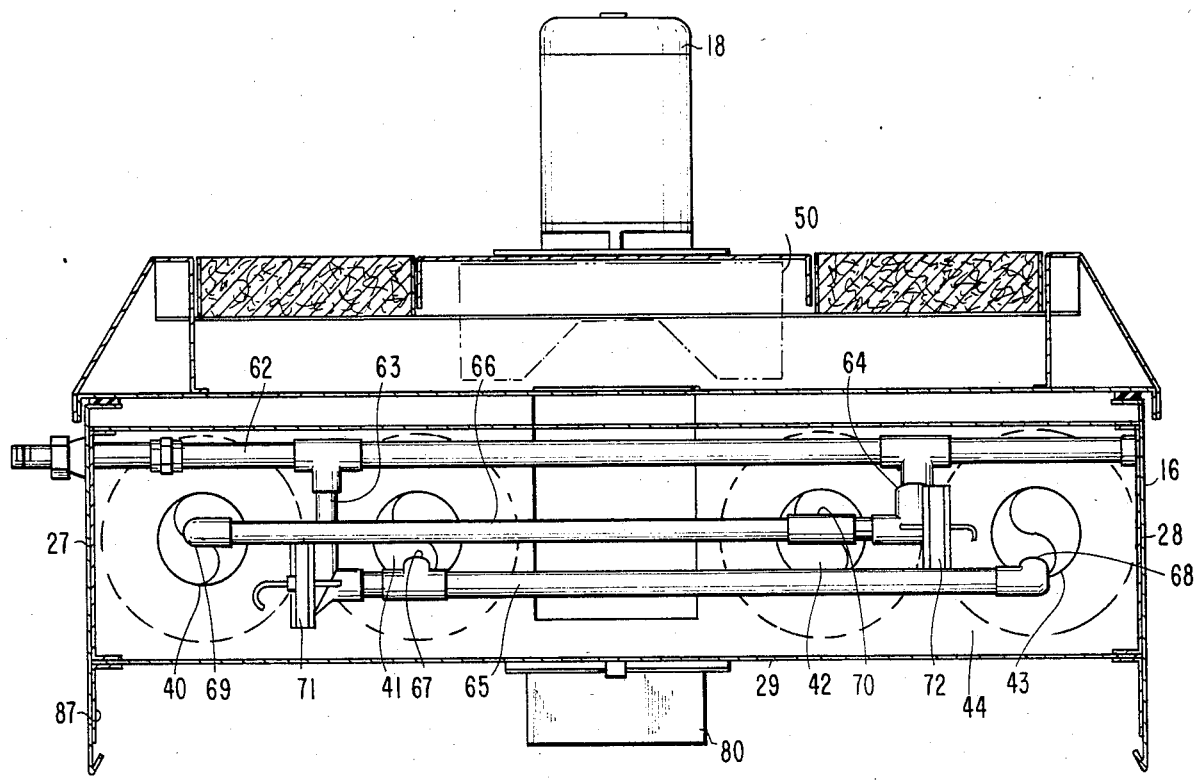
FIG. 3 is a cross-sectional view taken along line 3—3 of FIG. 2 and viewed in the direction of the arrows.
Figure 4:
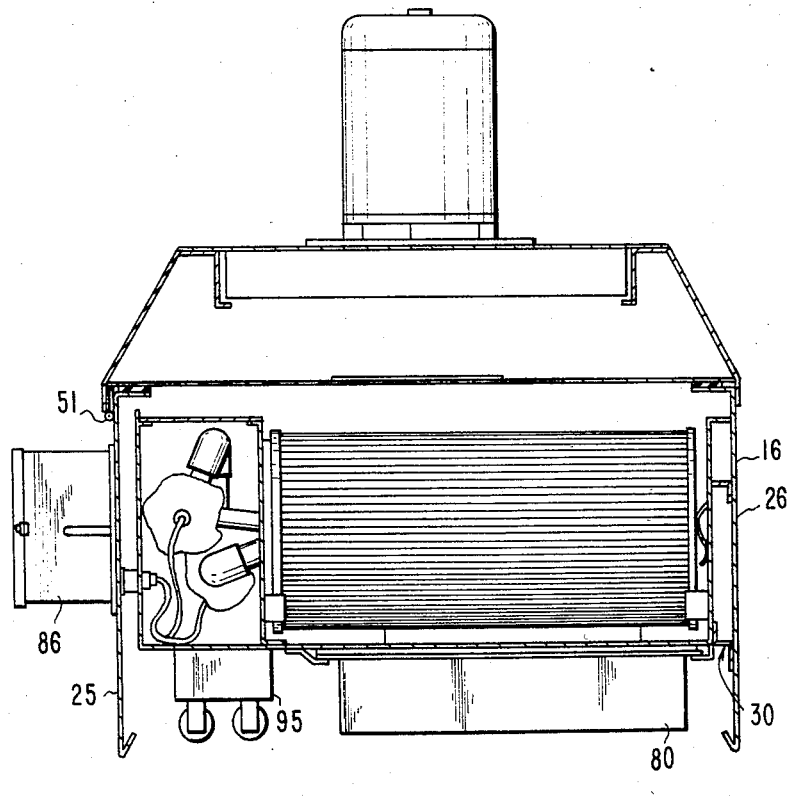
FIG. 4 is a cross-sectional view taken along line 4—4 of FIG. 2 and viewed in the direction of the arrows.

Housing member 16 (FIGS. 3 and 4) includes a front wall 25 and back wall 26 fixedly secured to end walls 27 and 28. A bottom wall 29 extends across and between the four walls 25 through 28 with the exception that a slot 30 is formed immediately adjacent back wall 26 to form an entrance opening allowing the air beneath the hood containing the noxious fumes to flow into the filters contained within the hood. A perforated wall 31 (FIG. 1) extends across slot 30 to limit flow of solid material into the passage 34.

A pair of vertical walls 32 and 33 (FIG. 2) extend between end walls 27 and 28 and form cooperatively with bottom wall 29 a holder for removably holding the four cylindrical filters 21 through 24. Wall 33 is spaced apart from back wall 26 thereby forming an air passage 34 extending from entrance or slot 30 past a pair of spark deflectors 35 and 36 and eventually into the filter holder. Deflector 35 is cantileveredly mounted to back wall 26 and has a distal end spaced apart from wall 33, whereas deflector 36 is cantileveredly mounted to wall 33 and has a distal end spaced apart from the back wall 26. As a result, passage 34 has a serpentine configuration insuring that any sparks contained within the air passing through perforated wall 31 impinge upon spark deflectors 35 and 36 preventing the sparks from reaching the paper board constructed cylindrical filters. The air passing through passage 34 is then directed downwardly into the holder formed between walls 32 and 33 impinging upon the outer cylindrical surface of filters 21 through 24.

Cylindrical filters 21 through 24 are conventional in construction and are commercially available from the TDC Filter Manufacturing Company, Evanston, Ill. Each cylindrical filter includes a pair of disc shaped end walls 37 and 38 between which extend conventional corrugated paper board construction material. The center portion 39 of each cylindrical filter is hollow thereby allowing the air impinging upon the outer cylindrical surface of the filter to pass through the filter and into the hollow center portion 39. Wall 32 includes four apertures 40 through 43 (FIG. 3), respectively arranged with the hollow center portions of filters 24 through 21. Wall 32 is spaced apart from front wall 25 forming an air chamber 44 (FIG. 2) into which the filtered air from the hollow center portions 39 past. An exit opening 45 provided in wall 32 between filters 22 and 23 is provided to allow the filtered air within chamber 44 to escape. A pair of interior vertical walls 46 and 47 extend between walls 32 and 33 cooperatively forming with two interior horizontal intermediate walls 85 and 48, an intermediate air passage. Aperture 49 is provided in intermediate wall 48 and is positioned immediately beneath the blades 50 (FIG. 3) rotatably driven by the fan motor 18 mounted atop lid 17.

The lid extends across the entire top of rectangular housing frame 16 and may be pivoted about hinge 51 (FIG. 4) securing the lid to the front wall 25. A pair of exit openings 52 and 53 (FIG. 1) lead to and between the lid and aperture 49. The lid includes a bottom wall which extends across the entire underside of the lid separating apart the chamber 44 and filters 21 through 24 and allowing air flow to the charcoal filters 19 and 20 only through aperture 49. Thus, operation of fan motor 18 results in air from beneath the exhaust hood flowing into an air passage first through slot 30 and past deflectors 35 and 36 into the cylindrical filter holder. The air pulled by the fan blades then enters each cylindrical filter in a radial direction exiting each cylindrical filter through the hollow center portions passing through apertures provided in wall 32 and into chamber 44. The filtered air exits chamber 44 through opening 45 and then passes through aperture 49 to a position beneath blades 50. The air is then forced through lid 17 exiting the moveable welding station through apertures 52 and 53 and through the charcoal filters 19 and 20 into the ambient air surrounding the moveable welding station. As the air containing the noxious fumes beneath the hood is expelled from the moveable welding station via filters 19 and 20, additional fresh air is pulled from the air surrounding the moveable welding station into the work area positioned beneath the hood and then passes through the filtering process described.

Charcoal filters 19 and 20 are conventional in design and are commercially available. The filters are received within rectangular holders provided in lid 17 adjacent exit openings 52 and 53. In order to change all filters, charcoal filters 19 and 20 may be pulled upwardly and exchanged with fresh filters whereas lid 17 may be pivoted about hinge 51 and cylindrical holders 21 through 24 exchanged with new filters. The cylindrical filters are held between walls 32 and 33 by means of filter support clips mounted to the walls. For example, a pair of clips 60 and 61 (FIG. 2) are fixedly attached to wall 33 each having a ledge arranged to supportingly receive the circumferentially extending edge of disc shaped end wall 38 of filter 22. Likewise, a second pair of clips are mounted to wall 32 and likewise supportingly receive the edge of the disc shaped end wall 37. Thus, filter 22 may be moved downwardly resting upon the pair of clips mounted to wall 33 and a pair of clips mounted to wall 32. A leaf spring 62 is mounted to wall 33 and located above clips 60 and 61 and positioned to contact end wall 38 of the filter and force the filter toward and against wall 32 thereby releasably holding the filter between walls 32 and 33. In order to remove the filters, the filters may simply be pulled upwardly overcoming the spring resistance of leaf spring 62.

A pulse cleaning tube 62 is mounted to end wall 27 and extends outwardly therefrom having a conventional fitting to attach to a source of pressurized air. Tube 62 extends through the length of chamber 44 (FIG. 3) and is in fluid communication by means of cross tubes 63 and 64, respectively, with a pair of air tubes 65 and 66. Air tube 65 includes two openings 67 and 68 which open, respectively, adjacent and into the hollow center portions of filters 23 and 21. Likewise, air tube 66 has a pair of openings 69 and 70 which open respectively adjacent and into the hollow center portions of filters 24 and 22. Openings 67 through 70 are formed by conventional right angle couplings attached to air tube 65 and 66 allowing the pressurized air within each air tube to escape outwardly. Conventional air operated valves 71 and 72 are mounted to tubes 65 and 66. By opening air valve 71, air is allowed to flow from tube 62 and into air tube 65 thereby escaping into the hollow interior portions of filters 23 and 21. Simultaneously with the opening of air valve 71, the second air valve 72 is closed preventing air flow through tube 66. Likewise, upon the opening of air valve 72 and the closing of air valve 71, pressurized air is directed through tube 62 and via tube 66 into the hollow center portions of filters 24 and 22. The air pressure applied into air tube 62 and exiting into the hollow center portions of each filter is between 80 to 100 psi and of a duration from 0.1 seconds to 2.0 seconds. Such pulses of air in a direction opposite to the normal radial air flow from passage 34 into the cylindrical filters results in the dislodging of foreign particulate matter contained within each cylindrical filter providing an automatic cleaning procedure. The pulse shocks of pressurized air exiting air tubes 65 and 66 are on the magnitude of from two to five times the air pressure of the air flowing in a normal radially inward direction through the cylindrical filters.

Figure 5:
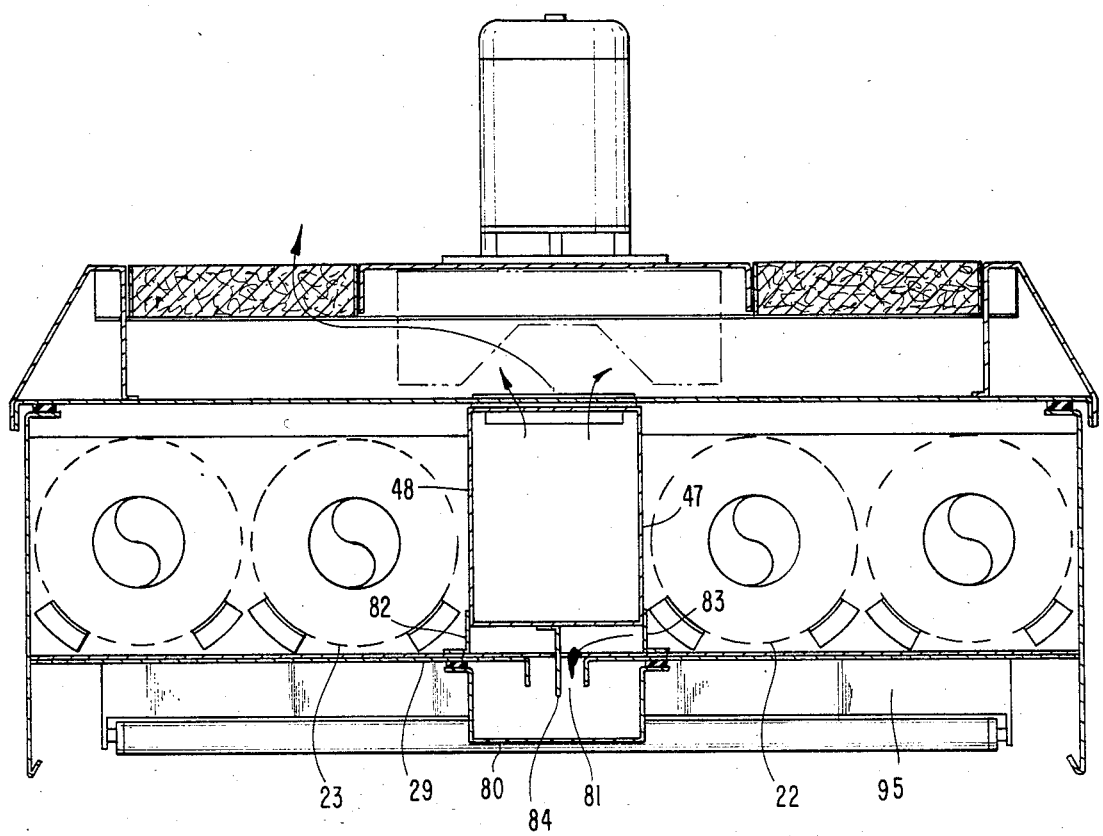
FIG. 5 is a cross-sectional view taken along line 5—5 of FIG. 2 and viewed in the direction of the arrows.

A dust box 80 is removably mounted to bottom wall 29 and is positioned beneath a slot 81 (FIG. 5) formed in the bottom wall 29 located between filters 22 and 23. Walls 46 and 47 each include reverse flow apertures 82 and 83 located between bottom wall 29 and intermediate wall 85 (FIG. 2) allowing the foreign particulate matter dislodged by the reverse air flow from each cylindrical air filter to flow beneath each cylindrical filter and through slot 81 into dust pan 80. It should be noted that each cylindrical filter 21 through 24 is positioned slightly above and spaced apart from bottom wall 29 to provide a suitable foreign particulate passage to apertures 82 and 83. A downwardly extending separator wall 84 is fixedly attached to the intermediate wall 85 and extends through slot 81 and into the dust pan preventing foreign particulate matter flow between a first group of filters 21 and 22 and a second group of filters 23 and 24.

Various conventional controls are provided on the moveable welding station including a conventional fluorescent light fixture 95 mounted to bottom wall 29 beneath chamber 44. Likewise, a conventional timing device and conventional controls are provided within box 86 affixed to the front wall 25. The timing device is operable to periodically pulse filters 21 and 23 and then filters 21 and 22 every two to ten minutes by opening and closing valves 71 and 72. In other words, filters 21 and 23 are first pulsed and then filters 22 and 24 are pulsed.

Further, curtains are mounted beneath the hood and extend downwardly on at least two sides thereof preventing air flow cross currents beneath the hood. Bracket 87 (FIG. 3) extends downwardly from the front wall, back wall and end walls allowing a flexible curtain produced from a material such as plastic to be hung thereon in conventional fashion with the curtain then extending downwardly to the ground. In one embodiment the curtain extended downwardly only from end walls 27 and 28. In such a case, it is necessary to locate the hood adjacent a building wall to insure that the air flow into slot 30 results from air flowing from beneath the hood and not immediately from the area surrounding the welding station. In another embodiment, a curtain was suspended from bracket 87 at the end walls 27 and 28 and also the back wall 26 forming a three-sided enclosure defining the work area. A work desk or bench area is provided beneath the hood upon which the work is to be accomplished.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An air treatment and recycler for a single welding station within a building comprising:
   a frame forming a hood and configured to form a single welding station, said frame including an air passage having an entrance opening within said single welding station and an exit opening on said frame and into ambient air within said building:
   curtain means mounted to said frame and depending therefrom surrounding said single welding station on at least two sides thereof;
   a motorized fan mounted to said frame operable to draw air from within said single welding station through said passage and forcing said air outwardly of said frame recirculating air between said welding station and ambient air within said building;
   first filter means mounted in said passage and operable to filter air moving in a normal direction therethrough;
   pulsing means operably associated with said filter means and operable to direct pulses of pressurized air flow in an direction opposite from said normal direction and of a magnitude greater than said air moving in said normal direction through said filter means unlodging foreign particulate matter from said filter means; and, holding means mounted to said frame and positioned to receive said foreign particulate matter from said filter means as said pulsing means unlodges same.

2. The recycler of claim 1 wherein:
said first filter means include a plurality of cylindrical filters arranged into a first group and a second group removably mounted to said frame, said filters include hollow center portions;
said passage directs air from said welding station radially into each of said filters exiting said filters from said hollow center portions.

3. The recycler of claim 2 wherein:
said pulsing means includes air tubes extending adjacent each of said hollow center portions of said filters and including control means operable to sequentially direct air pulses first into said hollow center portions of said first group of filters and then into said hollow center portions of said second group of filters; and further comprising:
back charge baffle means mounted to said frame operable to limit movement of said foreign particulate between said filters.

4. The recycler of claim 3 and further comprising:
second filter means mounted to said frame adjacent said exit; and
timing means connected to said pulsing means being operable to periodically operate said pulsing means.

5. The recycler of claim 4 wherein:
said first filter means includes pleated board filter construction within said filters; and,
said second filter means includes a plurality of charcoal filters.

6. The recycler of claim 5 wherein:
said pulses or of a magnitude in excess of 50 psi.

7. The recycler of claim 2 wherein:
said frame includes a first filter holder to removably hold said filters and a plurality of upstanding members depending therefrom to support said holder above said single welding station, said frame forming an air chamber adjacent said filter holder which opens into said chamber allowing air flow from said center portions into said chamber, said air passage extends from said single welding station into said holder radially through said filters and via said center portions into said chamber.

8. The recycler of claim 7 and further comprising:
second filter means mounted to said frame adjacent said exit with said fan operable to force air from said chamber through said second filter means.

9. The recycler of claim 8 wherein:
said pulsing means includes air tubes extending through said chamber adjacent each of said hollow center portions of said filters and including control means operable to sequentially direct said pulses first into said hollow center portions of said first group of filters and then into said hollow center portions of said second group of filters;
said holding means is mounted beneath said filter holder which has a slot through which said foreign particulate matter passes from said filters into said holding means; and further comprising:
back charge baffle means mounted to said frame operable to limit movement of said foreign particulate matter between filters.

10. An air treatment and recycler for a work station comprising:

a frame forming a hood and configured to form a work station, said frame including an air passage having an entrance opening within said work station and an exit opening on said frame;
curtain mounting means on said frame to receive curtains depending therefrom to at least partially surround said work station;
exhaust means mounted to said frame operable to draw air from within said work station through said passage and forcing said air outwardly of said frame recirculating air within said work station;
first filter means mounted in said passage and operable to filter air moving in a normal direction therethrough;
pulsing means operably associated with said filter means and operable to direct pulses of pressurized air flow in an direction opposite from said normal direction and of a magnitude greater than said air moving in said normal direction through said filter means unlodging foreign particulate matter from said filter means; and,
holding means mounted to said frame and positioned to receive said foreign particulate matter from said filter means as said pulsing means unlodges same.

11. The recycler of claim 10 wherein:
said first filter means include a plurality of cylindrical filters arranged into a first group and a second group removably mounted to said frame;
said passage directs air from said work station into each of said filters;
said pulsing means includes air tubes extending adjacent each of said filters to sequentially direct said pulses first into said first group of filters and then into said second group of filters; and further comprising:
back charge baffle means mounted to said frame operable to block movement of said foreign particulate matter between said filters.

12. The recycler of claim 11 wherein:
said frame includes a first filter holder to removably hold said filters and a plurality of upstanding members depending therefrom to support said holder above said work station, said frame forming an air chamber adjacent said filter holder which opens into said chamber allowing air flow from said filters into said chamber, said air passage extends from said work station into said filter holder through said filters and then into said chamber, said pulsing means includes air tubes extending through said chamber adjacent each of said filters to sequentially direct said pulses first into said first group of filters and then into said second group of filters;
said holding means is mounted beneath said filter holder which has a slot through which said foreign particulate matter passes from said filters into said holding means.

13. An exhaust hood for recirculating air from beneath the hood to the air surrounding the hood comprising:
upstanding frame members to support a curtain defining the work area;
a hood frame mounted atop said frame members with said hood frame including an air passage with an air entrance opening beneath said hood frame and an air outlet opening outwardly thereof;
air moving means in communication with said air passage and operable to move air therethrough drawing air surrounding the hood into the work area and then expelling same into the air surrounding said hood;

filters mounted to said hood frame and operable to filter air moved by said air moving means through said air passage;

pulsing means positioned adjacent said filters and operable to pulsatingly force air through said filters in a direction opposite to air moved by said air moving means dislodging foreign matter in said filters; and, back charge baffle means operable to limit foreign matter flow between filters.

14. The exhaust hood of claim 13 wherein:

said hood frame includes a first filter holder to removably hold said filters, said hood frame forming an air chamber adjacent said holder which opens therein allowing air flow from said chamber into said holder, said air passage extends from said work area into said holder and radially through said filters and into said chamber, said pulsing means includes air tubes extending through said chamber adjacent each of said filters to sequentially direct air pulses first into at least one of said filters and then into at least another of said filters.

15. The exhaust hood of claim 14 and further comprising:

holding means positioned to catch said foreign matter dislodged from said filters;

curtain means extending down from said hood frame adjacent said work area and limiting cross air flow therethrough.

16. The exhaust hood of claim 15 wherein:

said air pulses are of a magnitude of at least 50 psi and of a duration of at least 0.1 second.

* * * * *